US012690841B2

(12) United States Patent
Howard et al.

(10) Patent No.: US 12,690,841 B2
(45) Date of Patent: Jul. 28, 2026

(54) ULTRAPORTABLE ULTRASOUND

(71) Applicant: FUJIFILM SONOSITE, INC.,
Bothell, WA (US)

(72) Inventors: Christopher Howard, Seattle, WA
(US); Derek Jensen, Mountlake
Terrace, WA (US); **Sebastian
Tomaszewski**, Kenmore, WA (US);
Marnie Hamp, Kirkland, WA (US);
Craig Chamberlain, Seattle, WA (US)

(73) Assignee: FUJIFILM SONOSITE, INC.,
Bothell, WA (US)

( * ) Notice: Subject to any disclaimer, the term of this
patent is extended or adjusted under 35
U.S.C. 154(b) by 95 days.

(21) Appl. No.: 18/419,410

(22) Filed: Jan. 22, 2024

(65) Prior Publication Data

US 2025/0235185 A1        Jul. 24, 2025

(51) Int. Cl.
*A61B 8/00* (2006.01)
*G16H 10/60* (2018.01)

(52) U.S. Cl.
CPC .......... *A61B 8/4427* (2013.01); *A61B 8/4433*
(2013.01); *A61B 8/463* (2013.01); *A61B 8/465*
(2013.01); *A61B 8/5215* (2013.01); *G16H
10/60* (2018.01)

(58) Field of Classification Search
CPC ... A61B 8/4405; A61B 8/4411; A61B 8/4427;
A61B 8/4433; A61B 8/4472; A61B
8/461; A61B 8/462; A61B 8/463; A61B
8/465; A61B 8/5215; A61B 8/565; G16H
10/60
See application file for complete search history.

(56) References Cited

U.S. PATENT DOCUMENTS

2019/0328229 A1* 10/2019 Sanchez ................. H04N 7/144

* cited by examiner

*Primary Examiner* — Mark D Remaly
(74) *Attorney, Agent, or Firm* — Womble Bond Dickinson
(US) LLP

(57) ABSTRACT

Embodiments of ultrasound systems and methods for using
the same are disclosed. In some embodiments, an ultrasound
system includes a mobile computing device configured to be
wirelessly coupled to the ultrasound scanner and display an
ultrasound image based on reflections of ultrasound, and a
docking station to support the mobile computing device. The
ultrasound system also includes a processor system config-
ured to enable the ultrasound system with additional ultra-
sound features when the mobile computing device is sup-
ported by the docking station, which are unavailable to the
ultrasound system when the mobile computing device is
unsupported by the docking station.

19 Claims, 12 Drawing Sheets

100

200

300
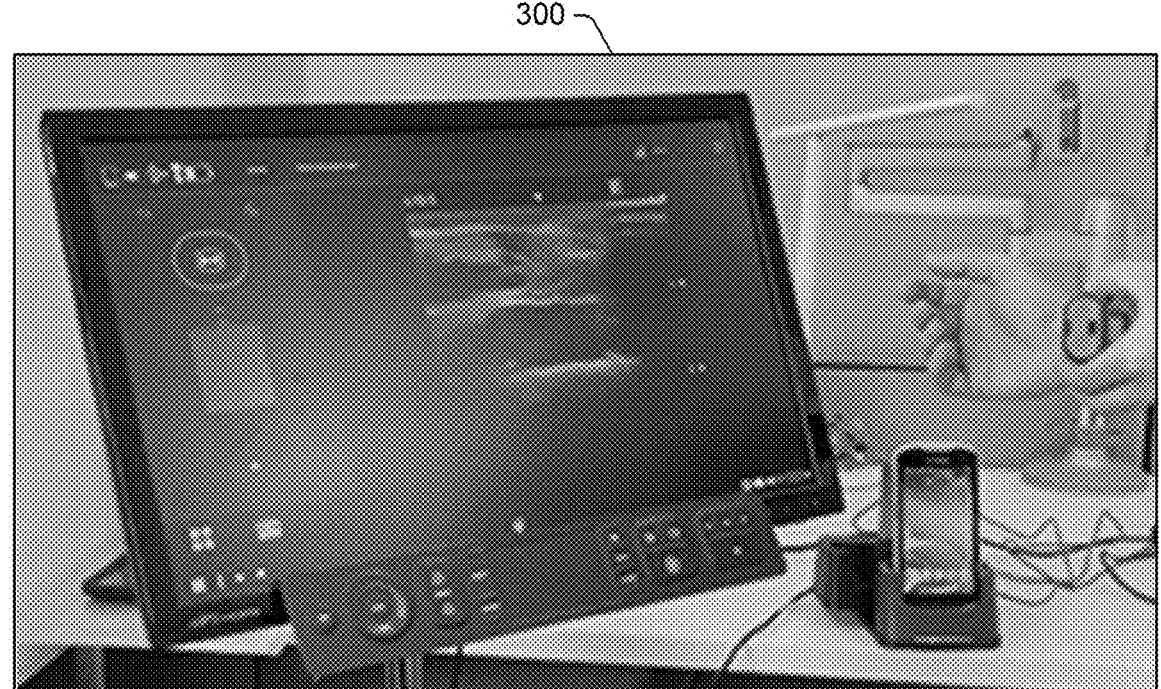
302
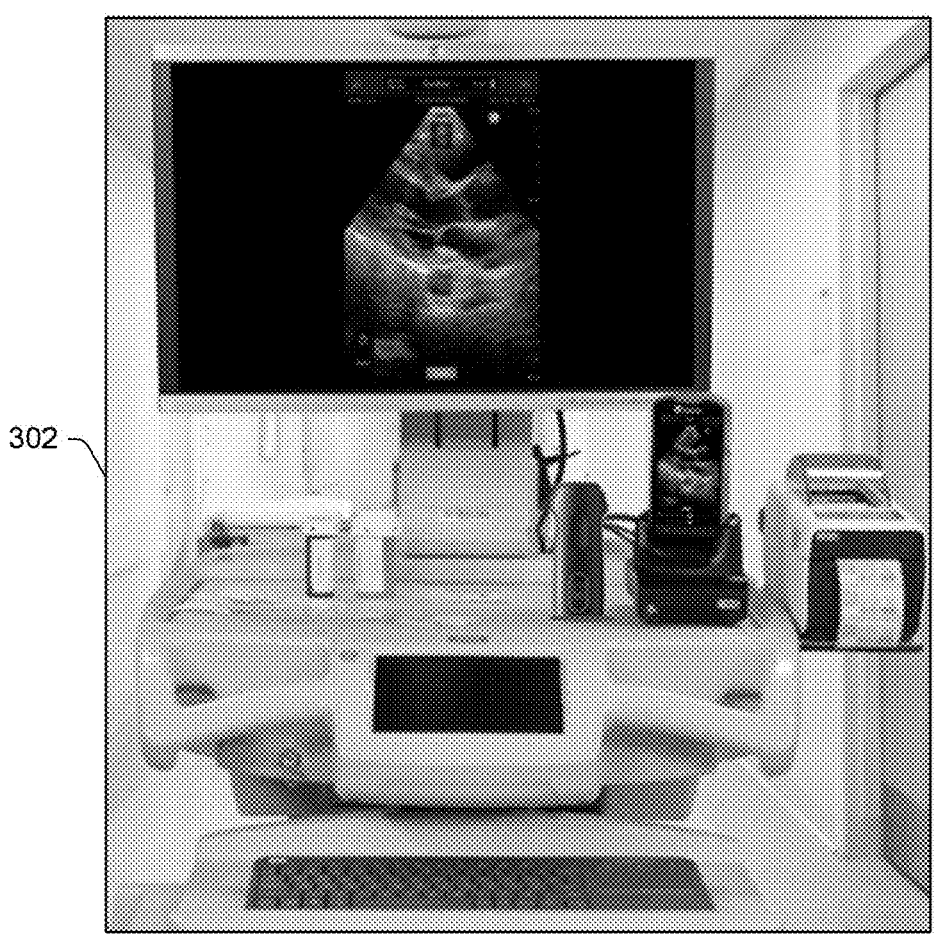
FIG. 3A

304 ⁓

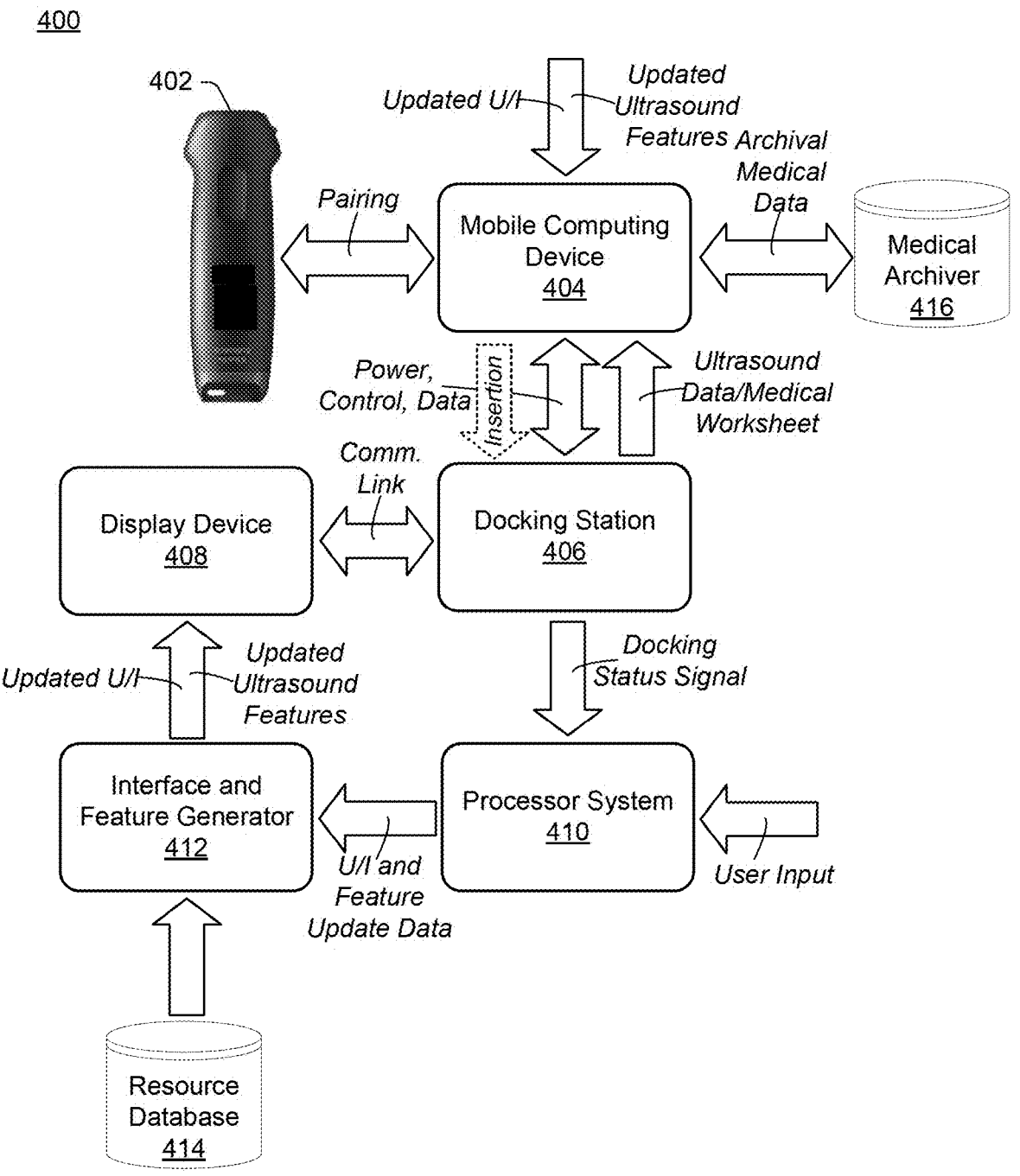

400

402

Updated U/I    Updated Ultrasound Features

Archival Medical Data

Pairing

Mobile Computing Device
404

Medical Archiver
416

Power, Control, Data

Insertion

Ultrasound Data/Medical Worksheet

Comm. Link

Display Device
408

Docking Station
406

Updated U/I    Updated Ultrasound Features

Docking Status Signal

Interface and Feature Generator
412

U/I and Feature Update Data

Processor System
410

User Input

Resource Database
414

FIG. 4

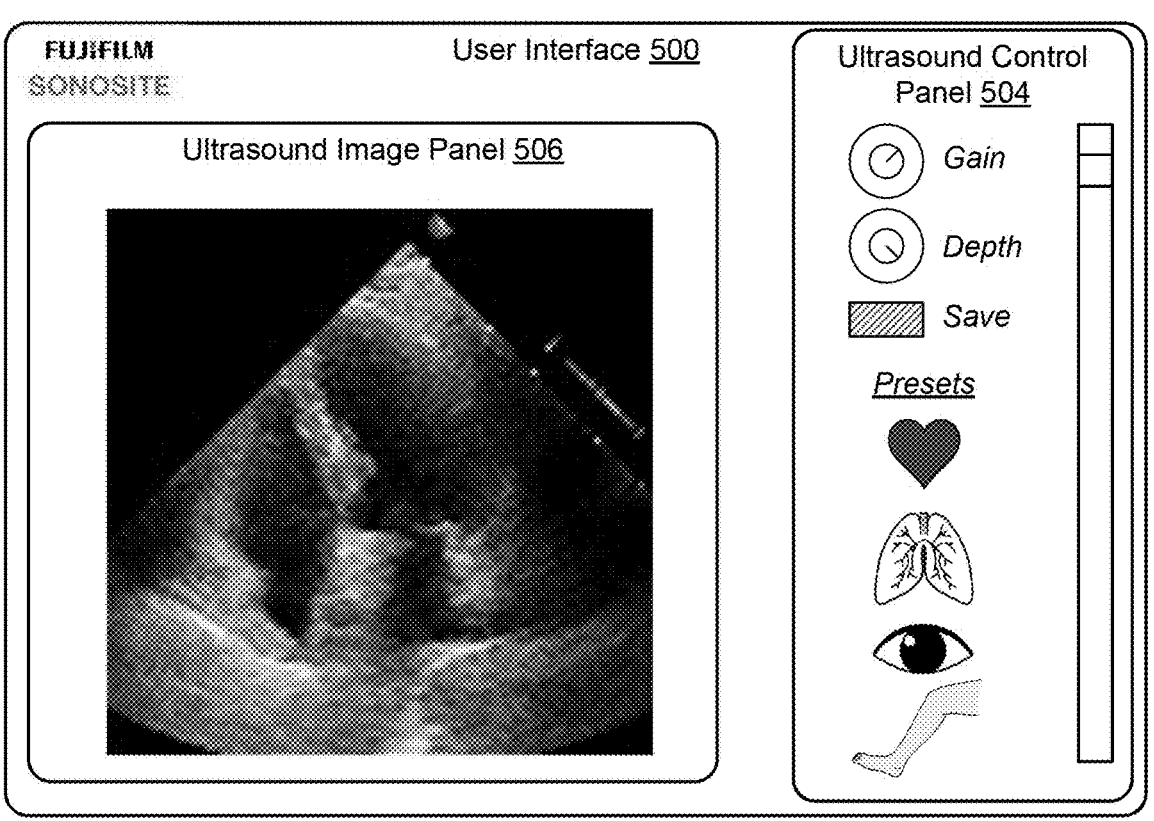
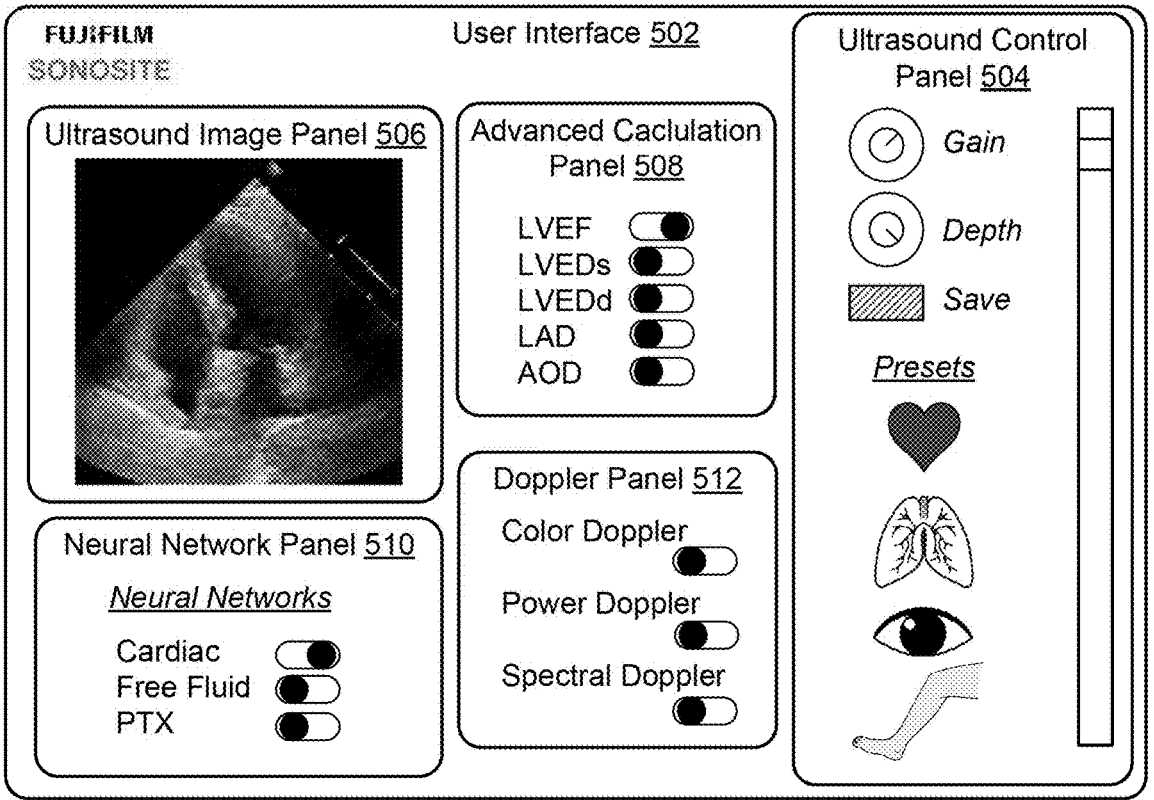
FIG. 5

700

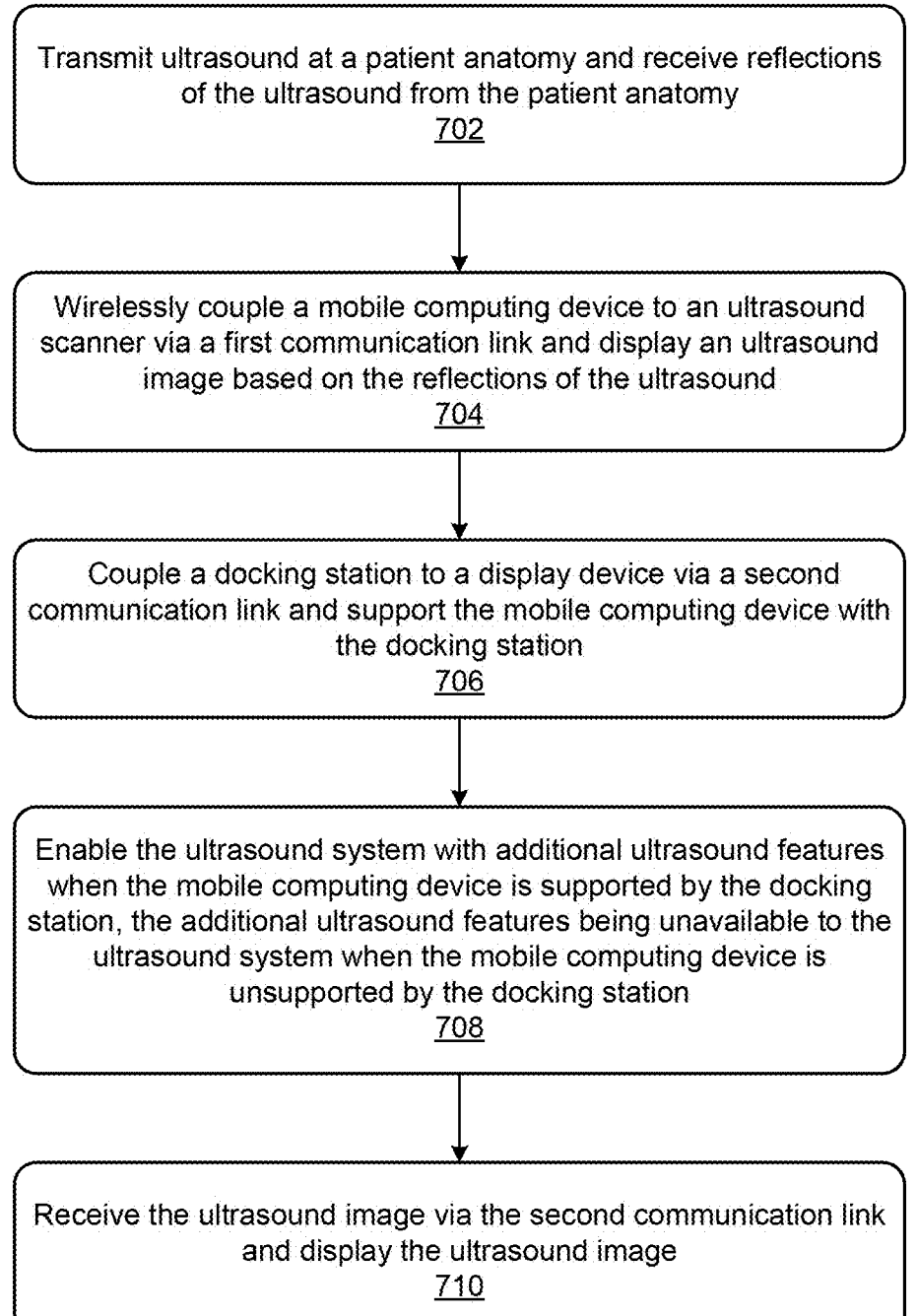

Transmit ultrasound at a patient anatomy and receive reflections of the ultrasound from the patient anatomy
702

Wirelessly couple a mobile computing device to an ultrasound scanner via a first communication link and display an ultrasound image based on the reflections of the ultrasound
704

Couple a docking station to a display device via a second communication link and support the mobile computing device with the docking station
706

Enable the ultrasound system with additional ultrasound features when the mobile computing device is supported by the docking station, the additional ultrasound features being unavailable to the ultrasound system when the mobile computing device is unsupported by the docking station
708

Receive the ultrasound image via the second communication link and display the ultrasound image
710

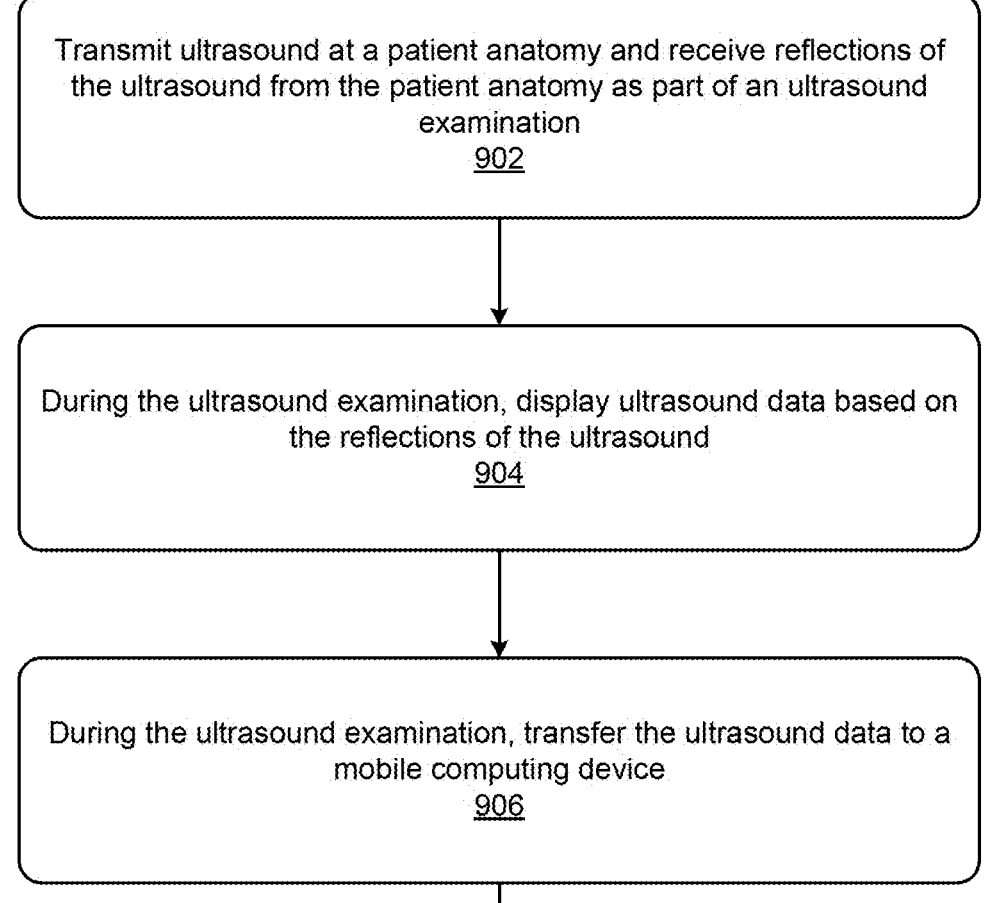

Transmit ultrasound at a patient anatomy and receive reflections of the ultrasound from the patient anatomy as part of an ultrasound examination
902

During the ultrasound examination, display ultrasound data based on the reflections of the ultrasound
904

During the ultrasound examination, transfer the ultrasound data to a mobile computing device
906

Display, on the mobile computing device, the ultrasound data for at least one of labeling and measurement subsequent to the ultrasound examination
908

ULTRAPORTABLE ULTRASOUND

FIELD OF THE INVENTION

Embodiments disclosed herein relate to ultrasound systems. More specifically, embodiments disclosed herein are related to a portable ultrasound system that has different functionality and/or operates differently when communicably coupled to a mobile computing device and/or a docking station.

BACKGROUND

Ultrasound systems can generate ultrasound images by transmitting sound waves at frequencies above the audible spectrum into a body, receiving echo signals caused by the sound waves reflecting from internal body parts, and converting the echo signals into electrical signals for image generation. Because they are non-invasive and non-ionizing, ultrasound systems are used ubiquitously, and come in various shapes and sizes. For instance, a radiology department may have a large, dedicated system that is not portable, whereas an emergency department may have a smaller ultrasound system that is portable for use at the point of care. Some of these point-of-care systems are referred to as ultraportable ultrasound systems, as they can include highly portable components, such as an ultrasound scanner that is wirelessly coupled to a handset (e.g., a smartphone or tablet). These ultraportable ultrasound systems can be easily and quickly deployed.

However, most ultraportable ultrasound systems have limited feature sets, often due to their limited processing resources that commonly are associated with small, portable devices. For instance, an ultraportable ultrasound system may be configured for basic ultrasound imaging, such as acquisition of B-mode and M-mode images, but may lack the rich feature sets commonly associated with cart-based or fixed ultrasound systems, e.g., the implementations of machine-learned models or neural networks that process the ultrasound images. Hence, an operator (e.g., physician, clinician, etc.) may need to switch from an ultraportable ultrasound system to a larger ultrasound system during an ultrasound examination to use the features that are not available with the ultraportable ultrasound system. Further, when ultrasound data is generated via the larger ultrasound system, such as label and measurement data, medical worksheet data, and the like, this data may not be available to the operator via the ultraportable ultrasound system. Accordingly, ultraportable ultrasound systems may not be suitable for some ultrasound examinations, thereby preventing patients from receiving the best care possible.

SUMMARY

Embodiments of ultrasound systems and methods for using the same are disclosed. In some embodiments, an ultrasound system includes an ultrasound scanner configured to transmit ultrasound at a patient anatomy and receive reflections of the ultrasound from the patient anatomy, a mobile computing device configured to be wirelessly coupled to the ultrasound scanner via a first communication link and display an ultrasound image based on the reflections of the ultrasound, and a docking station coupled to a display device via a second communication link and configured to support the mobile computing device. The ultrasound system also includes a processor system configured to enable the ultrasound system with additional ultrasound features when the mobile computing device is supported by the docking station, where the additional ultrasound features are unavailable to the ultrasound system when the mobile computing device is unsupported by the docking station. The display device is configured to receive the ultrasound image via the second communication link and display the ultrasound image.

In some other embodiments, the ultrasound system includes an ultrasound scanner configured to transmit ultrasound at a patient anatomy and receive reflections of the ultrasound from the patient anatomy, a mobile computing device configured to be coupled to the ultrasound scanner, a display device configured to display an ultrasound image that is generated based on the reflections of the ultrasound, and a docking station coupled to the display device and configured to support the mobile computing device. The mobile computing device is configured to display a first user interface for controlling the ultrasound system when supported by the docking station and a second user interface for controlling the ultrasound system when the mobile computing device is unsupported by the docking station.

In yet some other embodiments, the ultrasound system includes an ultrasound scanner configured to transmit ultrasound at a patient anatomy and receive reflections of the ultrasound from the patient anatomy as part of an ultrasound examination, and a display device. The display device is configured to, during the ultrasound examination, display ultrasound data based on the reflections of the ultrasound and transfer the ultrasound data to a mobile computing device. The mobile computing device is configured to display the ultrasound data for at least one of labeling and measurement subsequent to the ultrasound examination.

BRIEF DESCRIPTION OF THE DRAWINGS

The appended drawings illustrate examples and are, therefore, exemplary embodiments and not considered to be limiting in scope.

FIGS. 3A and 3B illustrate example ultraportable ultrasound systems in accordance with some embodiments.

FIG. 4 illustrates an example ultraportable ultrasound system in accordance with some embodiments.

FIG. 5 illustrates a first set of example user interfaces of an ultraportable ultrasound system in accordance with some embodiments.

FIG. 7 illustrates a first example method that can be performed by an ultraportable ultrasound system in accordance with some embodiments.

FIG. 9 illustrates a third example method that can be performed by an ultraportable ultrasound system in accordance with some embodiments.

DETAILED DESCRIPTION

In the following description, numerous details are set forth to provide a more thorough explanation of the present invention. It will be apparent, however, to one skilled in the art, that the present invention may be practiced without these specific details. In other instances, well-known structures and devices are shown in block diagram form, rather than in detail, in order to avoid obscuring the present invention.

Systems, devices, and techniques are disclosed herein for enabling ultraportable ultrasound systems with enhanced capabilities, including additional ultrasound features that are not available to the ultraportable ultrasound system in its basic form, e.g., when the ultraportable ultrasound system merely includes a wireless ultrasound scanner that is paired with a handset. The additional ultrasound features can become available upon the docking of a mobile device and can include, but are not limited to, the movement of information (e.g., user interface information, etc.) between two devices (e.g., between a mobile device and display device, etc.). Note that techniques disclosed herein are not limited to ultraportable ultrasound systems and can be used in other portable systems and kiosk-related systems.

Example Ultrasound Systems

Figure 1:
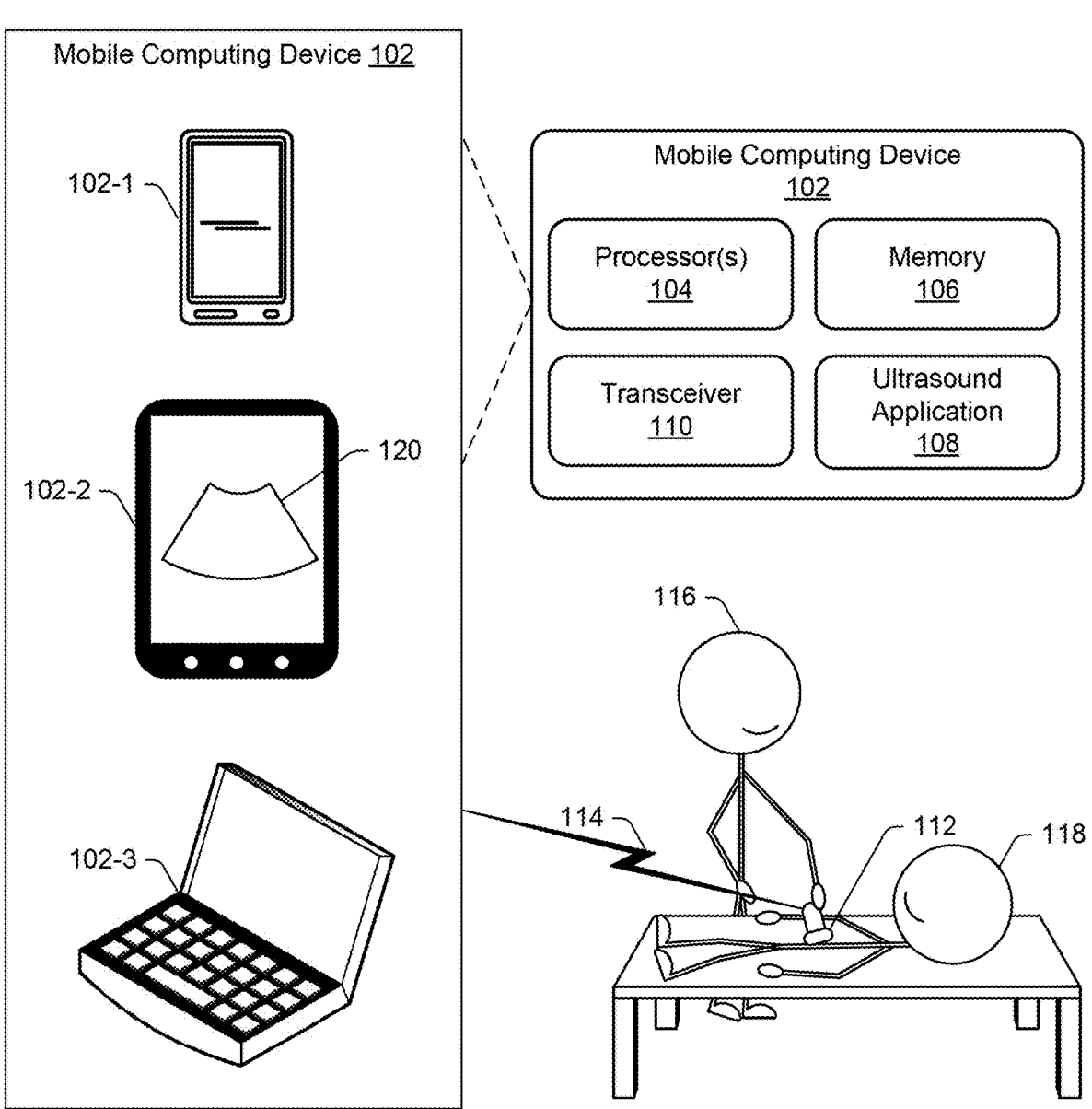
FIG. 1 illustrates some embodiments of an ultrasound system (e.g., an ultraportable ultrasound system) in an environment during an ultrasound examination.

FIG. 1 illustrates some embodiments of an ultrasound system (e.g., an ultraportable ultrasound system) in an environment 100 during an ultrasound examination. The ultrasound system includes a mobile computing device 102. The mobile computing device 102 can include any suitable mobile computing device, with the illustrated examples including a smartphone 102-1, a tablet 102-2, and a laptop 102-3 (collectively referred to as the mobile computing device 102), which can also be referred to as a handset. The mobile computing device 102 includes hardware, software, and firmware for performing the ultrasound examination, such as one or more processors 104 and one or more memories 106. In embodiments, the one or more memories 106 store instructions that when executed by the processor (s) 104 implement an ultrasound application 108 for performing the ultrasound examination, including controlling the ultrasound scanner 112 and viewing ultrasound images (e.g., the ultrasound image 120). The mobile computing device 102 also includes a transceiver 110 that can be used to communicate over a communication link 114 with the ultrasound scanner 112. In embodiments, the communication link 114 includes a wireless communication link so that the mobile computing device 102 and the ultrasound scanner 112 are wirelessly coupled, e.g., paired. Additionally or alternatively, the communication link 114 can include one or more cables as part of a wired communication link.

The ultrasound system also includes the ultrasound scanner 112, which can be referred to as an ultrasound probe, ultrasound transducer, and the like. In embodiments, the ultrasound scanner 112 is operated by an operator 116 (e.g., clinician, nurse, sonographer, etc.,) to transmit ultrasound at an anatomy of a patient 118 and receive reflections of the ultrasound from the patient anatomy as part of the ultrasound examination. The ultrasound system can generate the ultrasound image 120 based on the reflections, and the computing device 102 can display the ultrasound image 120.

Figure 2:
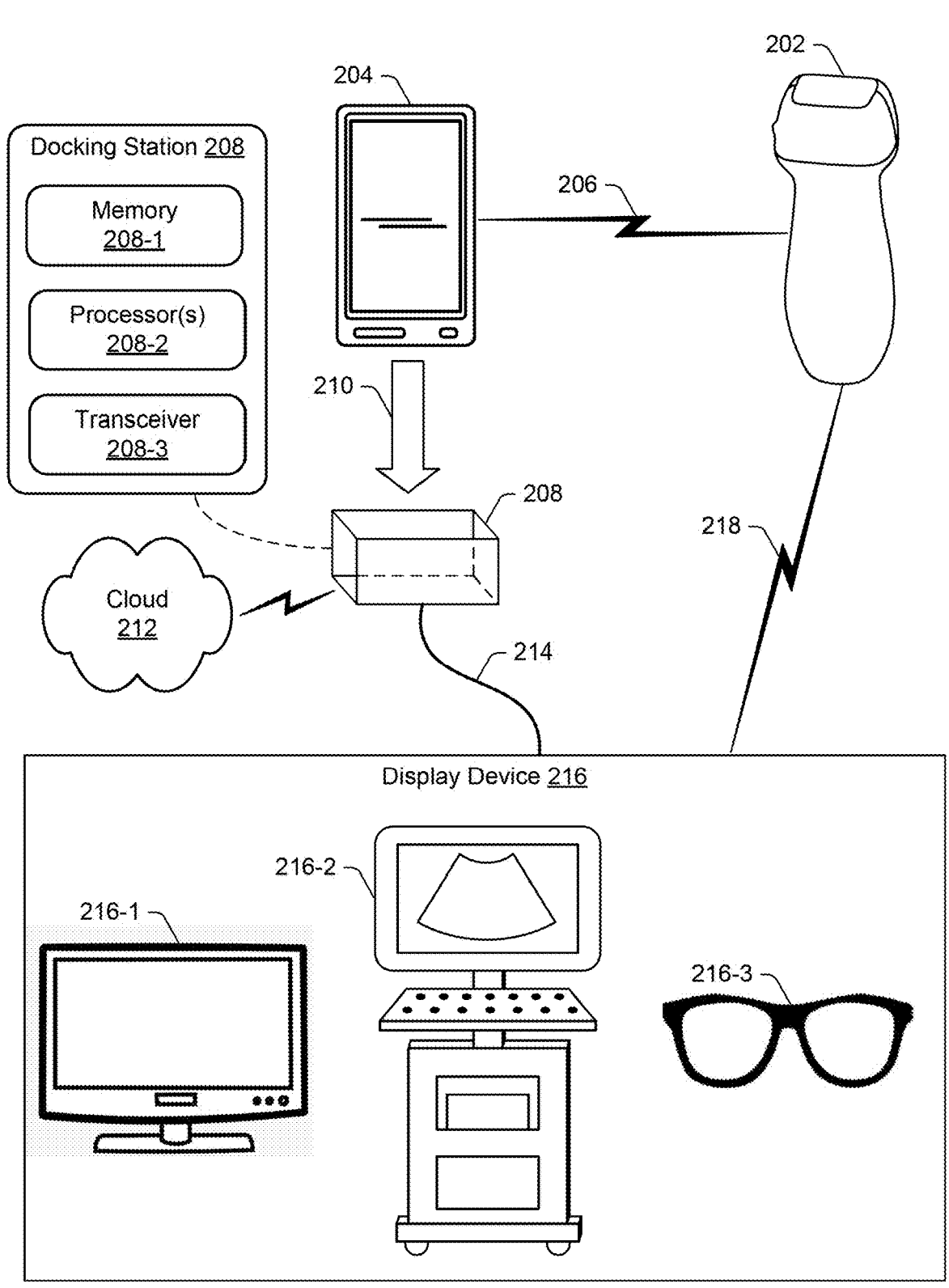
FIG. 2 illustrates an ultraportable ultrasound system in accordance with some embodiments.

FIG. 2 illustrates some embodiments of an ultraportable ultrasound system 200. Referring to FIG. 2, the ultraportable ultrasound system 200 includes an ultrasound scanner 202 (which is an example of the ultrasound scanner 112 in FIG.

1) and a mobile computing device 204 (which is an example of the mobile computing device 102 in FIG. 1). The ultrasound scanner 202 and the mobile computing device 204 are paired with one another, and are thus coupled via the communication link 206 (which is an example of the communication link 114 in FIG. 1). In embodiments, the communication link 206 includes a wireless communication link. Additionally or alternatively, the communication link 206 can include a wired communication link, including one or more cables.

The ultraportable ultrasound system 200 also includes a docking station 208 that can be configured to support (e.g., physically hold in place) the mobile computing device 204 when the mobile computing device 204 is inserted into the docking station 208. This insertion is illustrated by the arrow 210. The docking station 208 can be of any suitable form factor to support the mobile computing device 204, and is illustrated as a plain rectangular box in FIG. 2 for clarity. In some embodiments, the docking station 208 provides power to the mobile computing device 204 when it is docked (e.g., inserted into the docking station 208). Further, the docking station 208 can provide additional ultrasound resources to the ultraportable ultrasound system 200 when the mobile computing device 204 is supported by the docking station 208 (e.g., the mobile computing device 204 is docked). The additional ultrasound resources may not be available to the ultraportable ultrasound system 200 when the mobile computing device 204 is unsupported by the docking station 208 (e.g., it is not docked). The additional ultrasound resources can include, for example, but not limited to, advanced measurement capabilities (e.g., for cardiac parameters such as ejection fraction), implementations of machine-learned models (e.g. neural networks), advanced imaging modes (e.g., Doppler modes), and the like.

Hence, the docking station 208 can include any suitable hardware, software, and/or firmware to provide the additional ultrasound resources, including memory 208-1 and processors 208-2 that can execute instructions stored by the memory 208-1 to provide the additional ultrasound resources. The docking station 208 also includes a transceiver 208-3 for communicating with a cloud 212. Cloud 212 can include any network, network resources, server, database, and the like for providing resources, including the additional ultrasound resources, to the ultraportable ultrasound system 200. In some embodiments, the cloud 212 is maintained by a care facility (e.g., hospital, clinic, etc.) where the ultraportable ultrasound system 200 is used to perform ultrasound examinations. Additionally or alternatively, the cloud 212 can facilitate remote monitoring and management of one or more components of the ultraportable ultrasound system 200, such as the ultrasound scanner 202, the mobile computing device 204, the docking station 208, and the like.

The docking station 208 is coupled via a communication link 214 to a display device 216 of the ultraportable ultrasound system 200. The transceiver 208-3 can facilitate communication between the docking station 208 and the display device 216 over the communication link 214. The communication link 214 can include a wired connection (e.g., a cable) and/or a wireless connection to propagate data between the docking station 208 and the display device 216. The display device 216 can include any suitable device for displaying ultrasound data, illustrated examples of which include a monitor 216-1, an ultrasound machine 216-2, and smart glasses 216-3. These examples of the display device 216 are exemplary and meant to be non-limiting. In embodiments, the display device 216, e.g., the glasses 216-3, display ultrasound data (e.g., an ultrasound image) in an augmented reality (AR) or a virtual reality (VR) environment. In some embodiments, the additional ultrasound resources described above are provided to the ultraportable ultrasound system 200 by the display device 216.

In some embodiments, the mobile computing device 204 is configured to display a first user interface for controlling the ultraportable ultrasound system 200 when supported by the docking station 208 and a second user interface for controlling the ultraportable ultrasound system 200 when the mobile computing device 204 is unsupported by the docking station 208. For instance, the second user interface can include only basic ultrasound controls, such as controls for B-mode and M-mode imaging, and the first user interface can include advanced ultrasound imaging controls, such as controls for color Doppler, power Doppler, and spectral Doppler imaging. In some embodiments, a user can transfer components of a user interface displayed on the display device 216 to a user interface displayed by the mobile computing device 204 (and vice versa). For instance, a user can select a portion of a user interface on the display device 216, such as by drawing a boundary container around the portion to select the portion, and then perform a swipe gesture to an edge of the display device 216 to transfer the portion of the user interface to the mobile computing device 204. Additionally or alternatively, the user can transfer components of a user interface displayed on the mobile computing device 204 to a user interface displayed by the display device 216, such as with a selection trace and a swiping gesture.

In some embodiments, when the mobile computing device 204 is supported by the docking station 208, the ultraportable ultrasound system 200 can disable the communication link 206 between the mobile computing device 204 and the ultrasound scanner 202, and enable a communication link 218 between the ultrasound scanner 202 and the display device 216. Hence, the ultrasound scanner 202 can be paired with the display device 216.

In some embodiments, the ultraportable ultrasound system 200 facilitates the simultaneous use of multiple ultrasound scanners for use by different clinicians (not shown in FIG. 2 for clarity). For example, a first operator can operate a first ultrasound scanner that is coupled to the mobile computing device 204, a second operator can operate a second ultrasound scanner that is coupled to the docking station 208, and a third operator can operate a third ultrasound scanner that is coupled to the display device 216. Additionally or alternatively, one or more of the mobile computing device 204, the docking station 208, and the display device 216 can be simultaneously paired with multiple ultrasound scanners that are simultaneously operated by different operators. The display device 216 can display ultrasound data generated based on one or more of the ultrasound scanners. For instance, the smart glasses 216-3 can depict an AR or VR environment that overlays the data generated from two or more ultrasound scanners.

By providing the additional ultrasound resources to the ultraportable ultrasound system 200, e.g., from the cloud 212, the docking station 208, and/or the display device 216, the components of the ultraportable ultrasound system 200, including the mobile computing device 204 and the ultrasound scanner 202, can remain small in form factor and light weight, allowing them to be used for their intended purpose of ultra-portability. Further, the mobile computing device 204 and the ultrasound scanner 202 can consume less power than if they were required to implement the additional ultrasound resources. Hence, the ultrasound scanner 202 generates less heat, and thus can be used for longer scan times with shorter wait times between scans, resulting in better patient care. In some embodiments, the docking station 208 can be removably attached to the ultrasound scanner 202. Hence, the docking station 208 and the ultrasound scanner 202 can be transported as a single unit, to make it less susceptible to loss and/or theft. At the point of care, the docking station 208 can be quickly removed from the ultrasound scanner 202 for use.

Figure 3B:
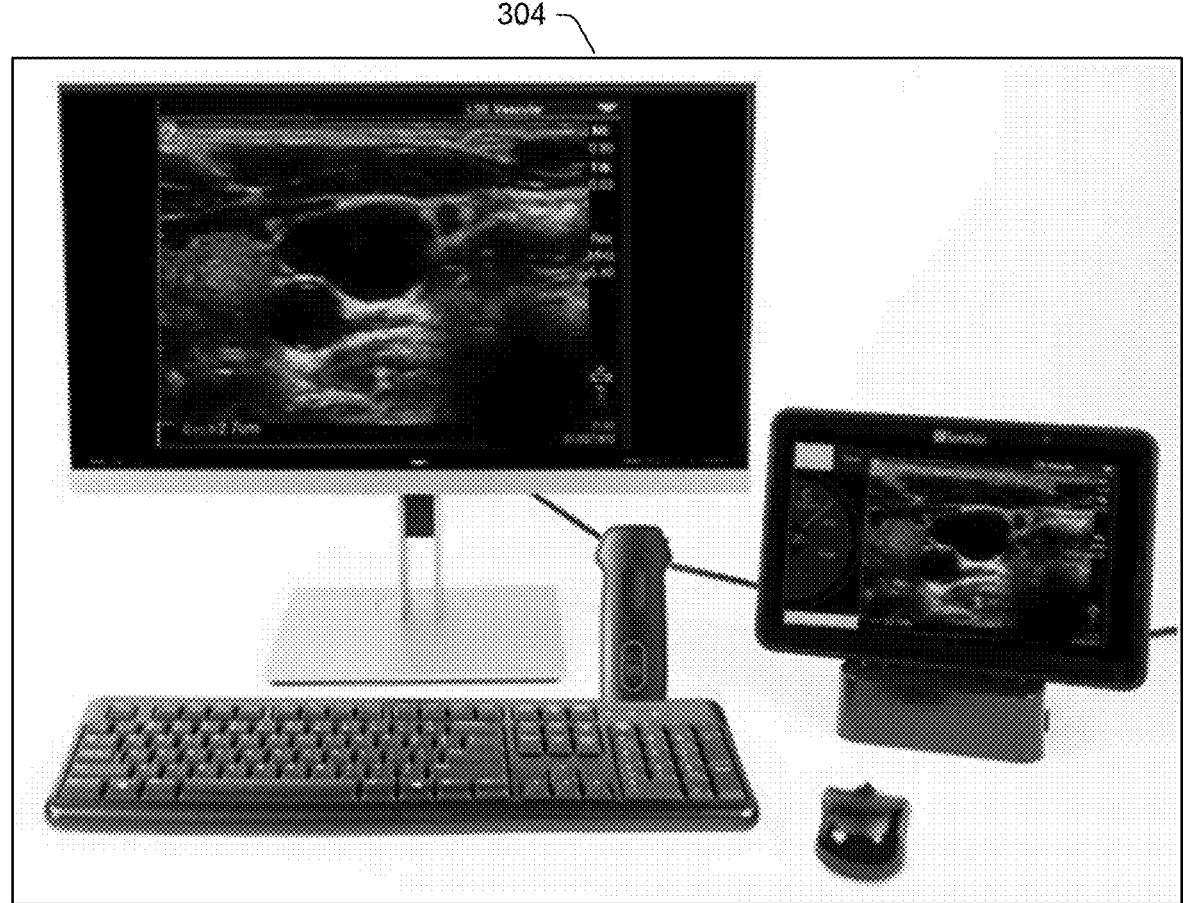

FIGS. 3A and 3B illustrate some embodiments of example ultraportable ultrasound systems. Referring to FIGS. 3A and 3B, the ultraportable ultrasound system 300 includes a mobile computing device that is a smartphone supported by a docking station. The ultraportable ultrasound system 300 also includes a display device that includes a monitor of an ultrasound machine on a stand. As shown, an operator is scanning their wrist, and the ultrasound image is displayed on the display device.

The ultraportable ultrasound system 302 includes a mobile computing device that is a smartphone supported by a docking station. The ultraportable ultrasound system 302 also includes a display device that includes a monitor of a cart-based ultrasound machine. An ultrasound image is simultaneously displayed on the display device and the mobile computing device.

The ultraportable ultrasound system 304 includes a mobile computing device that is a tablet supported by a docking station. The ultraportable ultrasound system 304 also includes a display device that includes a monitor of a desktop computer. An ultrasound image is simultaneously displayed on the display device and the mobile computing device. A user interface on the tablet can be used to control the wireless ultrasound scanner.

FIG. 4 illustrates some embodiments of an example ultraportable ultrasound system. Referring to FIG. 4, the ultraportable ultrasound system 400 includes an ultrasound scanner 402 that is paired with a mobile computing device 404. The ultrasound scanner 402 is an example of the ultrasound scanner 202 in FIG. 2, and the mobile computing device 404 is an example of the mobile computing device 204 in FIG. 2. The mobile computing device 404 is inserted into the docking station 406 so that it is supported by the docking station 406. The docking station 406 is an example of the docking station 208 in FIG. 2. The docking station 406 can provide power to the mobile computing device 404, as well as control data, such as from the display device 408, for controlling the ultrasound scanner 402. The mobile computing device 404 can provide data to the docking station 406, such as ultrasound image data generated by the mobile computing device 404 based on ultrasound reflections from the ultrasound scanner 402. The docking station can propagate the data to the display device 408 over a communication link between the docking station 406 and the display device 408. Hence, the display device 408 can display data (e.g., ultrasound data, user interface data, and the like) that is displayed on the mobile computing device, and vice versa.

The docking station 406 generates a docking status signal and provides it to the processor system 410. The docking status signal can include a binary indicator that indicates when the mobile computing device 404 is supported by, or docked with, the docking station 406. When the processor system 410 determines, based on the docking status signal, that the mobile computing device 404 is docked with the docking station 406, the processor system 410 can determine update data to update an ultrasound feature of the ultraportable ultrasound system 400, and/or a user interface displayed on one or both of the mobile computing device 404 and the display device 408. For example, the processor system 410 can receive a user input via a user interface displayed on the display device 408 to move a user interface component from the user interface of the display device 408 to a user interface displayed on the mobile computing device 404. In another example, the user input can include a selection to enable an additional ultrasound feature, such as a machine-learned model to generate an inference (e.g., an object segmentation, a probability of object detection, a classification label, etc.) based on an ultrasound image generated by the ultraportable ultrasound system 400. In some embodiments, the processor system determines what user interface and ultrasound feature updates to make, based on the user inputs and/or automatically made by the ultra-portable ultrasound system 400, and provides the update data to the interface and feature generator 412.

The interface and feature generator 412 receives the update data for the user interfaces and/or ultrasound features and retrieves the necessary resources from the resource database 414 to generate an updated user interface and/or updated ultrasound features. In some embodiments, the resource database 414 is included in the docking station 406. Additionally or alternatively, the resource database 414 can be included in a system that is separate from the ultraport-able ultrasound system 400, such as, for example, a cloud-based or other remotely-located server. The docking station 406 can retrieve the resources from the cloud-based server and store them in memory reserved for the resource database 414 that is local to the ultraportable ultrasound system 400, e.g., in a memory of the docking station 406. In some embodiments, the resource database 414 is included in the display device 408. In some embodiments, the interface and feature generator 412 provides an updated user interface and/or additional ultrasound features to one or both of the display device 408 and the mobile computing device 404.

In some embodiments, the updated user interface includes a medical worksheet and/or ultrasound data that is trans-ferred from the display device 408 to the mobile computing device 404. For example, a user can select to transfer the data from a user interface of the display device 408 to a user interface of the mobile computing device 404. The display device 408 can propagate the updated user interface over the communication link to the docking station 406, and the docking station 406 can provide the updated user interface to the mobile computing device 404. Hence, a medical worksheet can be transferred from the display device 408 (e.g., an ultrasound machine) during an ultrasound exami-nation to the mobile computing device 404, so that the medical worksheet can be viewed and edited on the mobile computing device 404 after the ultrasound examination is completed. The operator can then complete their study of a patient after the patient is examined, and send the completed report via the mobile computing device 404 to a medical archiver 416. Further, the mobile computing device 404 can obtain archival medical data from the medical archiver 416 before or during an ultrasound examination, and transfer this data via the docking station 406 to the display device 408 for display during the ultrasound examination.

Although not shown for clarity in FIG. 4, in some embodiments, the display device 408 can be in direct communication with the mobile computing device 404 with-out transferring data through the docking station 406. For instance, the ultraportable ultrasound system 400 can omit the docking station 406. The display device 408 can be configured to, during the ultrasound examination, display ultrasound data based on the reflections of the ultrasound received by the ultrasound scanner 402. The display device can then, during the ultrasound examination, transfer the ultrasound data to the mobile computing device 404. In some embodiments, the mobile computing device 404 can be configured to display the ultrasound data for at least one of labeling and measurement subsequent to the ultrasound examination.

Thus, in some embodiments, these transfers of data described above as well as others described herein can allow for the use of additional processing power made available by the device receiving the data to facilitate additional data processing and manipulation (e.g., image processing, access to graphics processing units (GPUs) not previously available for use, parallel processing, etc.). However, the additional processing is not limited to the device receiving the data and can include additional functionality that is made available to a device because the mobile computing device 404 is docked. For example, in some embodiments, after the mobile computing device 404 is being supported in the docking station 406, additional functionality is activated in the scanner 402.

Example User Interfaces

FIG. 5 illustrates example user interfaces 500 and 502 of an ultraportable ultrasound system in accordance with some embodiments of the present invention. The user interface 500 illustrates basic ultrasound features, and the user inter-face 502 illustrates advanced ultrasound features. The user interfaces 500 and 502 can be displayed by any suitable component of an ultraportable ultrasound system, including a mobile computing device (e.g., handset) and/or a display device (e.g., an ultrasound machine). In one example, the user interface 502 is displayed by a mobile computing device when the mobile computing device is supported by a docking station, and includes additional ultrasound features that are not available to the ultraportable ultrasound system when the mobile computing device is unsupported by the docking station. The mobile computing device can display the user interface 500 when the mobile computing device is unsupported by, or not docked to, the docking station.

In some embodiments, the user interface 500 can be displayed by the mobile computing device during an ultra-sound examination (e.g., when the mobile computing device is supported by the docking station), and the user interface 502 can be displayed by a display device (e.g., the ultra-sound machine). In still some other embodiments, the user interface 502 can be displayed by the mobile computing device during an ultrasound examination (e.g., when the mobile computing device is supported by the docking sta-tion), and the user interface 500 can be displayed by a display device (e.g., the ultrasound machine).

The user interface 500 illustrates basic ultrasound features for some embodiments, including an ultrasound control panel 504 with basic ultrasound controls for adjusting gain and depth, saving an image, and selecting examination presets. In some embodiments, the examination presets are represented by selectable icons for a cardiac examination, a respiratory examination, an ocular examination, and a mus-cular-skeletal examination. These examination presets, when selected, can configure the ultrasound machine with predetermined values of gain and depth, and other imaging parameters (e.g., beamformer settings and transducer fre-quency). The user interface 500 also includes an ultrasound image panel 506 for displaying an ultrasound image. In some embodiments, control of the ultrasound system using the user interface 500 is limited to B-mode imaging.

In contrast to the user interface 500, for some embodi-ments, the user interface 502 illustrates advanced ultrasound features that can be enabled when a mobile computing device is supported by a docking station. The user interface 502 includes the ultrasound control panel 504 and the ultrasound image panel 506 of the user interface 500, but also includes an advanced calculation panel 508, a neural network panel 510, and a Doppler panel 512. The advanced calculation panel 508 includes advanced ultrasound features that can be user selected. In the example in FIG. 5, the advanced calculation panel 508 displays cardiac calculations, since the cardiac neural network is selected in the neural network panel 510. The cardiac calculations that can be selected via the advanced calculation panel 508 include a left ventricle ejection fraction (LVEF), a left ventricular diameter at end-systole (LVEDs), a left ventricular diameter at end-diastole (LVEDd), a left atrial diameter (LAD), and an aortic diameter (AOD). The LVEF cardiac calculation is selected in the example in FIG. 5, and the other cardiac calculations are de-selected.

Note that in some embodiments, the user interface 500 displays one or more of the advanced calculation panel 508, the neural network panel 510, and the Doppler panel 512 but they are not selectable (or otherwise actionable) by the user. For example, these panels are grayed-out or referenced as being part of the user interface 500 but when the user tries to engage them, the mobile computing device takes no action. In some other embodiments, the user interface 500 displays an indication (e.g., a notification) to the user that such panels or other additional functionality are available if the mobile computing device is supported by a docking station.

In some embodiments, the neural network panel 510 includes neural networks that can be user selected, and that when implemented generate one or more inferences from an ultrasound image, e.g., the ultrasound image panel 506. Inferences can include an object classification label, a probability that an object is detected in the ultrasound image (e.g., free fluid), a probability that an image depicts an event (e.g., collapsed lung), a segmentation of an object, a segmentation image that includes the segmentation, and the like. In the example in FIG. 5, a cardiac neural network, a free-fluid neural network, and a pneumothorax neural network are available. The cardiac neural network is selected, while the free-fluid and pneumothorax neural networks are de-selected.

The Doppler panel 512 illustrates Doppler imaging modes that can be selected, and that are not available via the user interface 500. The Doppler panel 512 includes a color Doppler imaging mode, a power Doppler imaging mode, and a spectral Doppler imaging mode. None of these Doppler imaging modes are selected in the example of FIG. 5.

Note that in some embodiments, the user interface 500 and user interface 502 can be configured to present different, and potentially complementary, displays of information. For example, user interface 500 and user interface 502 can present two different sets of information (as opposed to one providing a subset of the information that is presented by the other) when the mobile computing device is supported by a docking station. The two different sets of information can provide a more comprehensive view of the information about a patient to the physician or clinician at the same time, which can be more useful in providing care to a patient.

Figure 6:
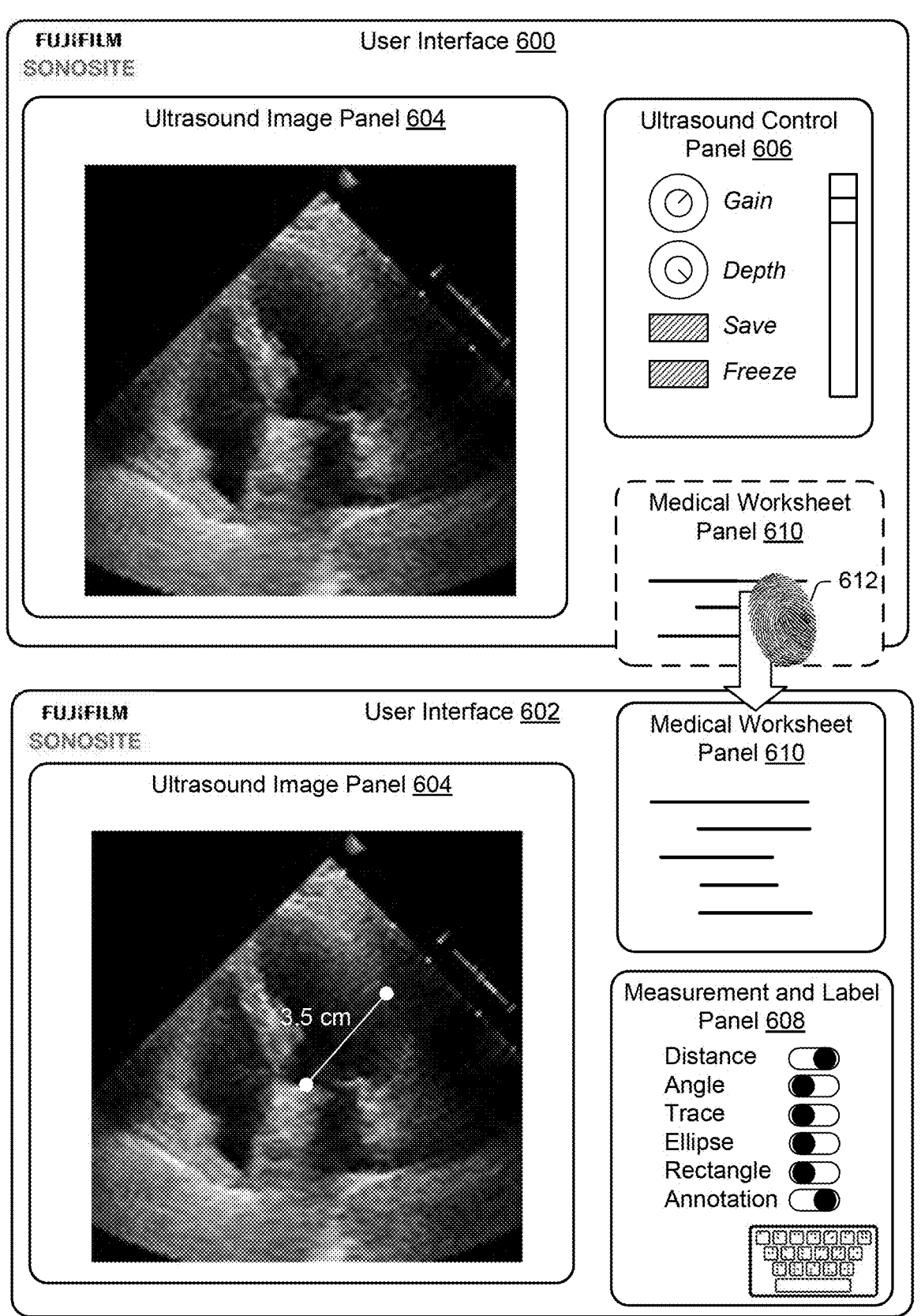
FIG. 6 illustrates a second set of example user interfaces of an ultraportable ultrasound system in accordance with some other embodiments.

FIG. 6 illustrates some embodiments of example user interfaces 600 and 602 of an ultraportable ultrasound system. The user interfaces 600 and 602 can be displayed by any suitable component of an ultraportable ultrasound system, including a mobile computing device (e.g., handset) and/or a display device (e.g., an ultrasound machine). In some embodiments, the user interface 600 is displayed by a display device (e.g., an ultrasound machine), and the user interface 602 is displayed by a mobile computing device (e.g., a handset).

Both user interfaces 600 and 602 include an ultrasound image panel 604 for displaying ultrasound images. In some embodiments, the user interface 600 includes an ultrasound control panel 606 with adjustments of gain and depth for configuring the ultraportable ultrasound system, as well as a save button for saving ultrasound images and/or video clips, and a freeze button for freezing an ultrasound image.

In some embodiments, the user interface 602 includes a measurement and label panel 608 that illustrates selectable tools for measuring, labeling, and annotating ultrasound images. The tools include a distance tool (e.g., a caliper), an angle tool to measure an angle, a trace tool to draw a trace, an ellipse tool to draw an ellipse (and/or draw minor and major axes of the ellipse), a rectangle tool to draw a box, and an annotation tool to add text via a pop-up keyboard. In the example in FIG. 6, the distance tool has been selected, and a distance in the ultrasound image panel 604 of the user interface 602 has been measured as 3.5 cm.

Further, a user has selected the medical worksheet panel 610 in the user interface 600 (indicated by the fingerprint 612) and moved the medical worksheet panel 610 to an edge of the user interface 600, such as with a swiping gesture indicated by the arrow overlaid on the medical worksheet panel 610 in the user interface 600. Responsive to the selection and swiping gestures, the ultraportable ultrasound system transfers the medical worksheet panel 610 from the user interface 600 to the user interface 602. Hence, a user can transfer the medical worksheet displayed in the medical worksheet panel 610 from a first device (e.g., an ultrasound machine), to a second device (e.g., a mobile computing device or handset). The user can then edit the medical worksheet via the second computing device, e.g., using the tools in the measurement and label panel 608, subsequent to the ultrasound examination. The user can then transfer the edited and commented medical worksheet to a medical archiver from the second computing device, via an "upload" button (not shown in FIG. 6 for clarity).

Example Procedures

FIG. 7 illustrates some embodiments of an example method 700 that can be performed by an ultraportable ultrasound system. Operations of the method can be performed by processing logic that can comprise hardware (circuitry, dedicated logic, etc.), software (such as is run on a general-purpose computer system or a dedicated machine), firmware, or combinations thereof. The processing logic can be included in an ultrasound system, such as an ultraportable ultrasound system. The ultrasound system can include an ultrasound scanner, a mobile computing device (e.g., a handset), a display device (e.g., an ultrasound machine), a docking station, and a processor system.

Referring to FIG. 7, the method 700 includes an ultrasound scanner transmitting ultrasound at a patient anatomy and receives reflections of the ultrasound from the patient anatomy (block 702). A mobile computing device is wirelessly coupled to the ultrasound scanner via a first communication link and displays an ultrasound image based on the reflections of the ultrasound (block 704). A docking station is coupled to a display device via a second communication link and supports the mobile computing device (block 706). A processor system enables the ultrasound system with additional ultrasound features when the mobile computing device is supported by the docking station (block 708). The additional ultrasound features are unavailable to the ultrasound system when the mobile computing device is unsupported by the docking station. The display device receives the ultrasound image via the second communication link and displays the ultrasound image (block 710).

In some embodiments, the processor system is implemented to, when the mobile computing device is supported by the docking station, disable the first communication link and enable a wireless coupling of the ultrasound scanner to the display device via a third communication link.

In some embodiments, the additional ultrasound features include a machine-learned model implemented to generate an inference based on the ultrasound image. The inference can include a segmentation of an object in the ultrasound image, a probability that the ultrasound image includes an object, a label, a classification, a representation of the ultrasound image in the style of another image, and the like.

In some embodiments, the docking station provides power to the mobile computing device when the mobile computing device is supported by the docking station. The docking station can include the processing system. The processing system can include processing resources implemented to generate the additional ultrasound features.

In some embodiments, the processor system is implemented to transfer a medical worksheet displayed on the display device to the mobile computing device, and the mobile computing device is implemented to display the medical worksheet. The transfer of the medical worksheet can be responsive to a user input. The ultrasound scanner can transmit the ultrasound and receive the reflections as part of an ultrasound examination, and the mobile computing device can display the medical worksheet when the ultrasound examination is completed and when the mobile computing device is unsupported by the docking station. Additionally or alternatively, the mobile computing device can, responsive to the transfer, populate the medical worksheet with ultrasound data generated based on the reflections of the ultrasound.

In some embodiments, the mobile computing device can display user interfaces for controlling the ultrasound system including a first user interface when the mobile computing device is supported by the docking station and a second user interface when the mobile computing device is unsupported by the docking station. In some embodiments, the display device can display a third user interface for controlling the ultrasound system, the third user interface including at least one ultrasound control that is not included in the first user interface. In some embodiments, the first user interface includes at least one ultrasound control that is not included in the second user interface. Additionally or alternatively, the second user interface can include at least one ultrasound control that is not included in the first user interface.

In some embodiments, the docking station is implemented to be removably attached to the ultrasound scanner for transport of the ultrasound scanner and the docking station as a single unit. For example, the docking station can snap onto a proximal end of the ultrasound scanner (e.g., the opposite end of the ultrasound scanner having the lens).

Figure 8:
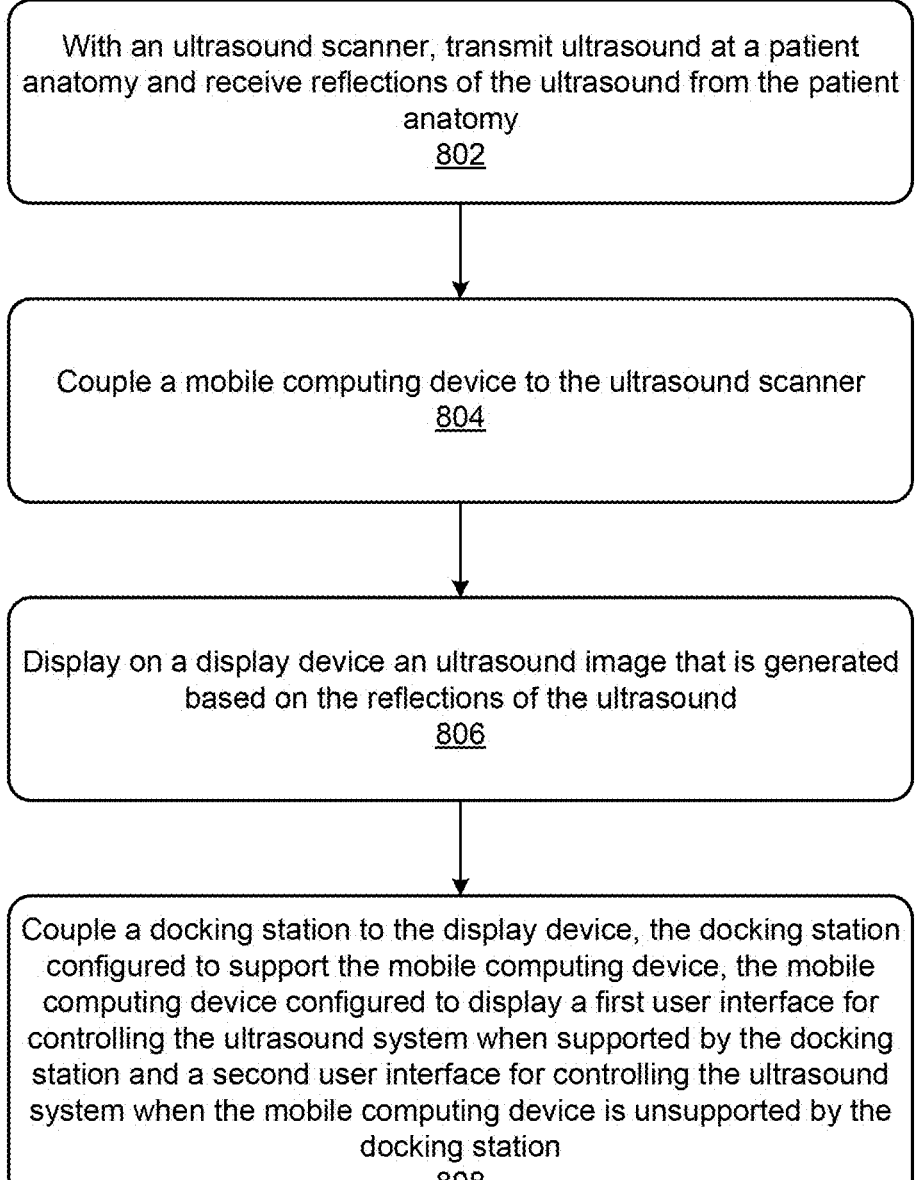
FIG. 8 illustrates a second example method that can be performed by an ultraportable ultrasound system in accordance with some embodiments.

FIG. 8 illustrates some embodiments of an example method 800 that can be performed by an ultraportable ultrasound system. Operations of the method can be performed by processing logic that can comprise hardware (circuitry, dedicated logic, etc.), software (such as is run on a general-purpose computer system or a dedicated machine), firmware, or combinations thereof. The processing logic can be included in an ultrasound system, such as an ultraportable ultrasound system. The ultrasound system can include an ultrasound scanner, a mobile computing device (e.g., a handset), a display device (e.g., an ultrasound machine), a docking station, and a processor system.

Referring to FIG. 8, the method 800 includes an ultrasound scanner transmitting ultrasound at a patient anatomy and receives reflections of the ultrasound from the patient anatomy (block 802). A mobile computing device is coupled to the ultrasound scanner (block 804). A display device displays an ultrasound image that is generated based on the reflections of the ultrasound (block 806). A docking station is coupled to the display device and supports the mobile computing device (block 808). The mobile computing device displays a first user interface for controlling the ultrasound system when supported by the docking station and a second user interface for controlling the ultrasound system when the mobile computing device is unsupported by the docking station.

In some embodiments, the second user interface includes at least one ultrasound control for controlling the ultrasound system, wherein the at least one ultrasound control is not included in the first user interface. Additionally or alternatively, the first user interface can include at least one ultrasound control for controlling the ultrasound system, wherein the at least one ultrasound control is not included in the second user interface.

In some embodiments, the display device displays a third user interface that displays a medical worksheet, and receives a user input. In some embodiments, responsive to the user input, the display device transfers the medical worksheet to the mobile computing device for display of the medical worksheet on the mobile computing device. Further, the mobile computing device can transfer the medical worksheet to a medical records archiver. Additionally or alternatively, the mobile computing device can receive medical records from the medical records archiver. These archived medical records can include HL7 and DICOM documents or other documents transferred or otherwise retrieved using a medical protocol. Note that by transferring documents and other information to the mobile computing device, the user of the mobile computing device (e.g., a physician, clinician, etc.) is able to take that information with them after de-docking from the docking station.

FIG. 9 illustrates some embodiments of an example method 900 that can be performed by an ultraportable ultrasound system. Operations of the method can be performed by processing logic that can comprise hardware (circuitry, dedicated logic, etc.), software (such as is run on a general-purpose computer system or a dedicated machine), firmware, or combinations thereof. The processing logic can be included in an ultrasound system, such as an ultraportable ultrasound system. The ultrasound system can include an ultrasound scanner, a mobile computing device (e.g., a handset), a display device (e.g., an ultrasound machine), a docking station, and a processor system.

Referring to FIG. 9, the method 900 includes an ultrasound scanner transmitting ultrasound at a patient anatomy and receives reflections of the ultrasound from the patient anatomy as part of an ultrasound examination (block 902). A display device, during the ultrasound examination, displays ultrasound data based on the reflections of the ultrasound (block 904). The display device, during the ultrasound examination, transfers the ultrasound data to a mobile computing device (block 906). The mobile computing device displays the ultrasound data for at least one of labeling and measurement subsequent to the ultrasound examination (block 908). In some embodiments, a docking station is implemented to, during the ultrasound examination, support the mobile computing device and couple the ultrasound scanner to the display device.

An Example Device

Figure 10:
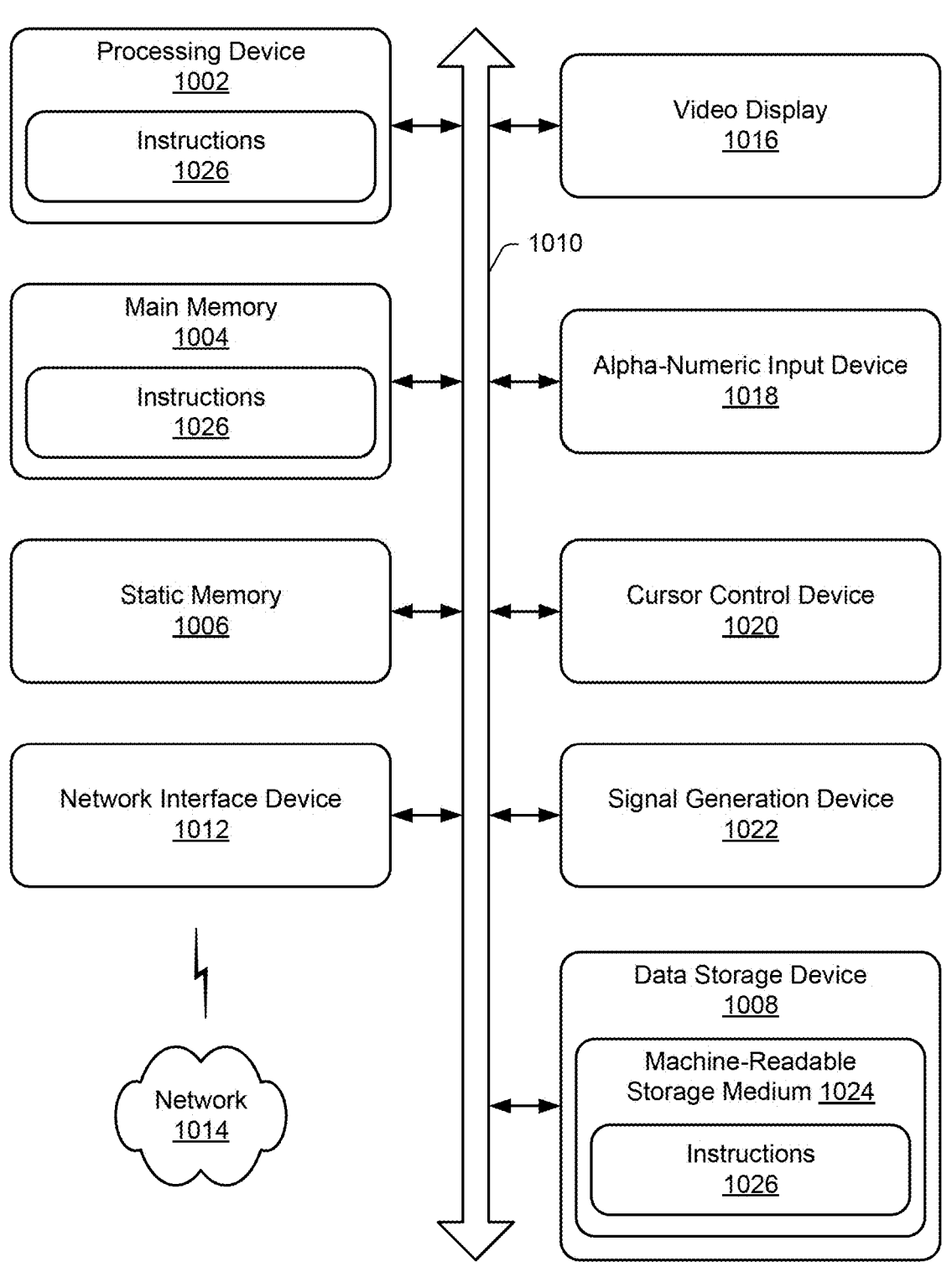
FIG. 10 illustrates a block diagram of an example computing device that can perform one or more of the operations described herein, in accordance with some embodiments.

FIG. 10 illustrates a block diagram of an example computing device 1000 that can perform one or more of the operations described herein, in accordance with some implementations. The computing device 1000 can be connected to other computing devices in a local area network (LAN), an intranet, an extranet, and/or the Internet. The computing device can operate in the capacity of a server machine in a client-server network environment or in the capacity of a client in a peer-to-peer network environment. The computing device can be provided by a personal computer (PC), a server computer, a desktop computer, a laptop computer, a tablet computer, a smartphone, an ultrasound machine, or any machine capable of executing a set of instructions (sequential or otherwise) that specify actions to be taken by that machine. Further, while only a single computing device is illustrated, the term "computing device" shall also be taken to include any collection of computing devices that individually or jointly execute a set (or multiple sets) of instructions to perform the methods discussed herein. In some embodiments, the computing device 1000 is one or more of an ultrasound machine, an ultrasound scanner, a docking station, a mobile computing device, a display device, an access point, and a packet-forwarding component.

The example computing device 1000 can include a processing device 1002 (e.g., a general-purpose processor, a programmable logic device (PLD), etc.), a main memory 1004 (e.g., synchronous dynamic random-access memory (DRAM), read-only memory (ROM), etc.), and a static memory 1006 (e.g., flash memory, a data storage device 1008, etc.), which can communicate with each other via a bus 1010. The processing device 1002 can be provided by one or more general-purpose processing devices such as a microprocessor, a central processing unit, or the like. In an illustrative example, the processing device 1002 comprises a complex instruction set computing (CISC) microprocessor, a reduced instruction set computing (RISC) microprocessor, a very long instruction word (VLIW) microprocessor, or a processor implementing other instruction sets or processors implementing a combination of instruction sets. The processing device 1002 can also comprise one or more special-purpose processing devices such as an application-specific integrated circuit (ASIC), a field programmable gate array (FPGA), a digital signal processor (DSP), a network processor, or the like. The processing device 1002 can be configured to execute the operations described herein, in accordance with one or more aspects of the present disclosure, for performing the operations and steps discussed herein.

The computing device 1000 can further include a network interface device 1012, which can communicate with a network 1014. The computing device 1000 also can include a video display unit 1016 (e.g., a liquid crystal display (LCD), an organic light-emitting diode (OLED), a cathode ray tube (CRT), etc.), an alphanumeric input device 1018 (e.g., a keyboard), a cursor control device 1020 (e.g., a mouse), and an acoustic signal generation device 1022 (e.g., a speaker, a microphone, etc.). In some embodiments, the video display unit 1016, the alphanumeric input device 1018, and the cursor control device 1020 can be combined into a single component or device (e.g., an LCD touch screen).

The data storage device 1008 can include a computer-readable storage medium 1024 on which can be stored one or more sets of instructions 1026 (e.g., instructions for carrying out the operations described herein, in accordance with one or more aspects of the present disclosure). The instructions 1026 can also reside, completely or at least partially, within the main memory 1004 and/or within the processing device 1002 during execution thereof by the computing device 1000, where the main memory 1004 and the processing device 1002 also constitute computer-readable media. The instructions can further be transmitted or received over the network 1014 via the network interface device 1012.

Various techniques are described in the general context of software, hardware elements, or program modules. Generally, such modules include routines, programs, objects, elements, components, data structures, and so forth that perform particular tasks or implement particular abstract data types. The terms "module," "functionality," and "component" as used herein generally represent software, firmware, hardware, or a combination thereof. In some aspects, the modules described herein are embodied in the data storage device 1008 of the computing device 1000 as executable instructions or code. Although represented as software implementations, the described modules can be implemented as any form of a control application, software application, signal-processing and control module, hardware, or firmware installed on the computing device 1000.

While the computer-readable storage medium 1024 is shown in an illustrative example to be a single medium, the term "computer-readable storage medium" should be taken to include a single medium or multiple media (e.g., a centralized or distributed database and/or associated caches and servers) that store the one or more sets of instructions. The term "computer-readable storage medium" shall also be taken to include any medium that is capable of storing, encoding, or carrying a set of instructions for execution by the machine and that causes the machine to perform the methods described herein. The term "computer-readable storage medium" shall accordingly be taken to include, but not be limited to, solid-state memories, optical media, and magnetic media.

Example Environment

Figure 11:
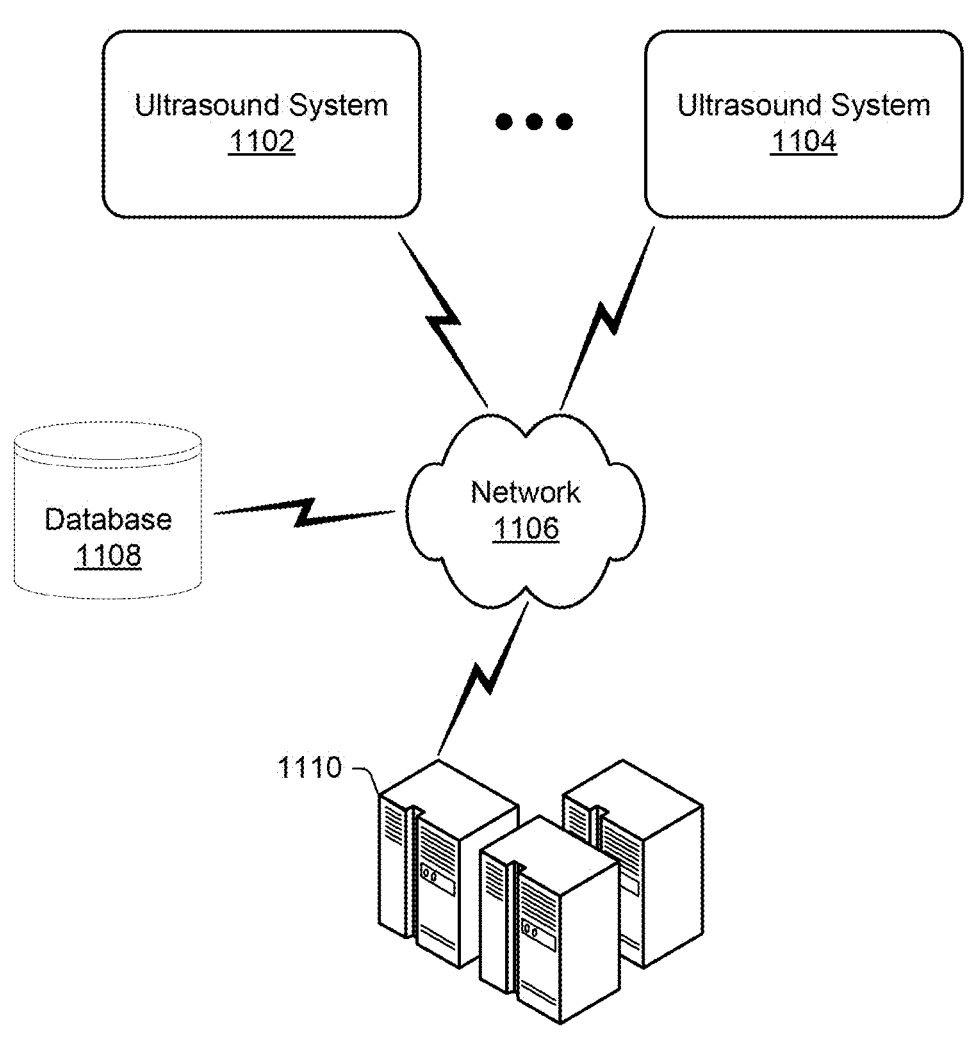
FIG. 11 illustrates an environment for an ultrasound system in accordance with some embodiments.

FIG. 11 illustrates an environment 1100 for an ultrasound system in accordance with some embodiments. The environment 1100 includes an ultrasound system 1102 and an ultrasound system 1104. Two example ultrasound systems 1102 and 1104 are illustrated in FIG. 11 for clarity. However, the environment 1100 can include any suitable number of ultrasound systems, such as the ultrasound systems maintained by a care facility or the department of a care facility. Generally, an ultrasound system can include any suitable device (e.g., a component of an ultrasound system). Examples devices of the ultrasound systems 1102 and 1104 include a charging station, an ultrasound machine, a display device (e.g., a tablet or smartphone), an ultrasound scanner, an ultrasound cart, and a display device. Other examples include a transducer cable, a transducer cable holder, a docking station, a scanner station configured to hold one or more ultrasound scanners, a needle guide, a battery for a wireless ultrasound scanner, a battery for an ultrasound machine, a registration system, and the like. The ultrasound systems 1102 and 1104 can include an ultraportable ultrasound system.

The ultrasound systems 1102 and 1104 can be in communication via the network 1106 as part of the environment 1100. The network 1106 can include any suitable network, such as a local area network, a wide area network, a near field communication network, the Internet, an intranet, an extranet, a system bus that couples devices or device components (e.g., in an ASIC, FPGA, or SOC), and combinations thereof. Accordingly, in embodiments, information can be communicated to the ultrasound systems 1102 and 1104 through the network 1106. For instance, the database 1108 can store instructions executable by a processor system of the ultrasound systems 1102 and 1104, and communicate the instructions via the network 1106. The database 1108 can store ultrasound resources and user interface components and share them with the ultrasound systems 1102 and 1104.

The environment 1100 also includes a server system 1110 that can implement any of the functions described herein. The server system 1110 can be a separate device from the ultrasound systems 1102 and 1104. Alternatively, the server system 1110 can be included in at least one of the ultrasound systems 1102 and 1104. In one example, the server system 1110 and the database 1108 are included in at least one of the ultrasound systems 1102 and 1104. In an example, the server system 1110 is implemented as a remote server system that is remote from (e.g., not collocated with) the ultrasound systems 1102 and 1104.

There are a number of example embodiments described herein.

Example 1 is an ultrasound system comprising: an ultrasound scanner configured to transmit ultrasound at a patient anatomy and receive reflections of the ultrasound from the patient anatomy; a mobile computing device configured to be wirelessly coupled to the ultrasound scanner via a first communication link and display an ultrasound image based on the reflections of the ultrasound; a docking station coupled to a display device via a second communication link and configured to support the mobile computing device; a processor system configured to enable the ultrasound system with additional ultrasound features when the mobile computing device is supported by the docking station, the additional ultrasound features being unavailable to the ultrasound system when the mobile computing device is unsupported by the docking station; and the display device configured to receive the ultrasound image via the second communication link and display the ultrasound image.

Example 2 is the ultrasound system of example 1 that may optionally include that the processor system is implemented to, when the mobile computing device is supported by the docking station, disable the first communication link and enable a wireless coupling of the ultrasound scanner to the display device via a third communication link.

Example 3 is the ultrasound system of example 1 that may optionally include that the additional ultrasound features include a machine-learned model implemented to generate an inference based on the ultrasound image.

Example 4 is the ultrasound system of example 1 that may optionally include that the docking station is implemented to provide power to the mobile computing device when the mobile computing device is supported by the docking station.

Example 5 is the ultrasound system of example 1 that may optionally include that the docking station includes the processing system, and the processing system includes processing resources implemented to generate the additional ultrasound features.

Example 6 is the ultrasound system of example 1 that may optionally include that the processor system is implemented to transfer a medical worksheet displayed on the display device to the mobile computing device, and the mobile computing device is implemented to display the medical worksheet.

Example 7 is the ultrasound system of example 6 that may optionally include that the transfer of the medical worksheet is responsive to a user input, the ultrasound scanner is implemented to transmit the ultrasound and receive the reflections as part of an ultrasound examination, and the mobile computing device is implemented to display the medical worksheet when the ultrasound examination is completed and when the mobile computing device is unsupported by the docking station.

Example 8 is the ultrasound system of example 8 that may optionally include that the mobile computing device is implemented to, responsive to the transfer, populate the medical worksheet with ultrasound data generated based on the reflections of the ultrasound.

Example 9 is the ultrasound system of example 1 that may optionally include that the mobile computing device is implemented to display user interfaces for controlling the ultrasound system including a first user interface when the mobile computing device is supported by the docking station and a second user interface when the mobile computing device is unsupported by the docking station.

Example 10 is the ultrasound system of example 9 that may optionally include that the display device is implemented to display a third user interface for controlling the ultrasound system, the third user interface including at least one ultrasound control that is not included in the first user interface.

Example 11 is the ultrasound system of example 9 that may optionally include that the first user interface includes at least one ultrasound control that is not included in the second user interface.

Example 12 is the ultrasound system of example 9 that may optionally include that the second user interface includes at least one ultrasound control that is not included in the first user interface.

Example 13 is the ultrasound system of example 1 that may optionally include that the docking station is implemented to be removably attached to the ultrasound scanner for transport of the ultrasound scanner and the docking station as a single unit.

Example 14 is an ultrasound system comprising: an ultrasound scanner configured to transmit ultrasound at a patient anatomy and receive reflections of the ultrasound from the patient anatomy; a mobile computing device configured to be coupled to the ultrasound scanner; a display device configured to display an ultrasound image that is generated based on the reflections of the ultrasound; a docking station coupled to the display device and configured to support the mobile computing device, the mobile computing device configured to display a first user interface for controlling the ultrasound system when supported by the docking station and a second user interface for controlling the ultrasound system when the mobile computing device is unsupported by the docking station.

Example 15 is the ultrasound system of example 14 that may optionally include that the second user interface includes at least one ultrasound control for controlling the ultrasound system, wherein the at least one ultrasound control is not included in the first user interface.

Example 16 is the ultrasound system of example 14 that may optionally include that the first user interface includes at least one ultrasound control for controlling the ultrasound system, wherein the at least one ultrasound control is not included in the second user interface.

Example 17 is the ultrasound system of example 14 that may optionally include that the display device is implemented to: display a third user interface that is configured to display a medical worksheet; receive a user input; and transfer, responsive to the user input, the medical worksheet to the mobile computing device for display of the medical worksheet on the mobile computing device.

Example 18 is the ultrasound system of example 17 that may optionally include that the mobile computing device is implemented to transfer the medical worksheet to a medical records archiver.

Example 19 is the ultrasound system of example 18 that may optionally include that the mobile computing device is implemented to receive medical records from the medical records archiver.

Example 20 is an ultrasound system comprising: an ultrasound scanner configured to transmit ultrasound at a patient anatomy and receive reflections of the ultrasound from the patient anatomy as part of an ultrasound examination; a display device configured to, during the ultrasound examination: display ultrasound data based on the reflections of the ultrasound; and transfer the ultrasound data to a mobile computing device, where the mobile computing device configured to display the ultrasound data for at least one of labeling and measurement subsequent to the ultrasound examination.

Example 21 is the ultrasound system of example 20 that may optionally include that a docking station implemented to, during the ultrasound examination, support the mobile computing device and couple the ultrasound scanner to the display device.

All of the methods and tasks described herein may be performed and fully automated by a computer system. The computer system may, in some cases, include multiple distinct computers or computing devices (e.g., physical servers, workstations, storage arrays, cloud computing resources, ultrasound systems, etc.) that communicate and interoperate over a network to perform the described functions. Each such computing device typically includes a processor (or multiple processors) that executes program instructions or modules stored in a memory or other non-transitory computer-readable storage medium or device (e.g., solid state storage devices, disk drives, etc.). The various functions disclosed herein may be embodied in such program instructions or may be implemented in application-specific circuitry (e.g., ASICs or FPGAs) of the computer system. Where the computer system includes multiple computing devices, these devices may, but need not, be co-located. The results of the disclosed methods and tasks may be persistently stored by transforming physical storage devices, such as solid-state memory chips or magnetic disks, into a different state. In some embodiments, the computer system may be a cloud-based computing system whose processing resources are shared by multiple distinct business entities or other users.

Depending on the embodiment, certain acts, events, or functions of any of the processes or algorithms described herein can be performed in a different sequence, can be added, merged, or left out altogether (e.g., not all described operations or events are necessary for the practice of the algorithm). Moreover, in some embodiments, operations or events can be performed concurrently, e.g., through multi-threaded processing, interrupt processing, or multiple processors or processor cores or on other parallel architectures, rather than sequentially.

The various illustrative logical blocks, modules, routines, and algorithm steps described in connection with the embodiments disclosed herein can be implemented as electronic hardware (e.g., ASICs or FPGA devices), computer software that runs on computer hardware, or combinations of both. Moreover, the various illustrative logical blocks and modules described in connection with the embodiments disclosed herein can be implemented or performed by a machine, such as a processor device, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A processor device can be a microprocessor, but in the alternative, the processor device can be a controller, microcontroller, or state machine, combinations of the same, or the like. A processor device can include electrical circuitry configured to process computer-executable instructions. In another embodiment, a processor device includes an FPGA or other programmable device that performs logic operations without processing computer-executable instructions. A processor device can also be implemented as a combination of computing devices, e.g., a combination of a DSP and a microprocessor, a plurality of microprocessors, one or more microprocessors in conjunction with a DSP core, or any other such configuration. Although described herein primarily with respect to digital technology, a processor device may also include primarily analog components. For example, some or all of the rendering techniques described herein may be implemented in analog circuitry or mixed analog and digital circuitry. A computing environment can include any type of computer system, including, but not limited to, a computer system based on a microprocessor, a mainframe computer, a digital signal processor, a portable computing device, a device controller, or a computational engine within an appliance, to name a few.

The elements of a method, process, routine, or algorithm described in connection with the embodiments disclosed herein can be embodied directly in hardware, in a software module executed by a processor device, or in a combination of the two. A software module can reside in RAM memory, flash memory, ROM memory, EPROM memory, EEPROM memory, registers, hard disk, a removable disk, a CD-ROM, or any other form of a non-transitory computer-readable storage medium. An exemplary storage medium can be coupled to the processor device such that the processor device can read information from, and write information to, the storage medium. In the alternative, the storage medium can be integral to the processor device. The processor device and the storage medium can reside in an ASIC. The ASIC can reside in a user terminal. In the alternative, the processor device and the storage medium can reside as discrete components in a user terminal.

Conditional language used herein, such as, among others, "can," "could," "might," "may," "e.g.," and the like, unless specifically stated otherwise, or otherwise understood within the context as used, is generally intended to convey that certain embodiments include, while other embodiments do not include, certain features, elements, or steps. Thus, such conditional language is not generally intended to imply that features, elements, or steps are in any way required for one or more embodiments or that one or more embodiments necessarily include logic for deciding, with or without other input or prompting, whether these features, elements or steps are included or are to be performed in any particular embodiment. The terms "comprising," "including," "having," and the like are synonymous and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list.

Disjunctive language such as the phrase "at least one of X, Y, or Z," unless specifically stated otherwise, is otherwise understood with the context as used in general to present that an item, term, etc., may be either X, Y, or Z, or any combination thereof (e.g., X, Y, or Z). Thus, such disjunctive language is not generally intended to, and should not, imply that certain embodiments require at least one of X, at least one of Y, and at least one of Z to each be present.

While the above detailed description has shown, described, and pointed out novel features as applied to various embodiments, it can be understood that various omissions, substitutions, and changes in the form and details of the devices or algorithms illustrated can be made without departing from the spirit of the disclosure. As can be recognized, certain embodiments described herein can be embodied within a form that does not provide all of the features and benefits set forth herein, as some features can be used or practiced separately from others. The scope of certain embodiments disclosed herein is indicated by the appended claims rather than by the foregoing description. All changes which come within the meaning and range of equivalency of the claims are to be embraced within their scope.

We claim:

1. An ultrasound system comprising:
an ultrasound scanner configured to transmit ultrasound at a patient anatomy and receive reflections of the ultrasound from the patient anatomy;
a mobile computing device configured to be wirelessly coupled to the ultrasound scanner via a first communication link and display an ultrasound image based on the reflections of the ultrasound;
a docking station coupled to a display device via a second communication link and configured to support the mobile computing device;
a memory coupled to the docking station;
a processor system coupled to the memory and configured to enable the ultrasound system with additional ultrasound features when the mobile computing device is supported by the docking station, the additional ultrasound features being unavailable to the ultrasound system when the mobile computing device is unsupported by the docking station, wherein the additional ultrasound features comprise a first neural network stored in the memory and a neural network control panel including a first neural network representation displayed on the display device that is implemented when being selected to generate a first inference based on the ultrasound image using the first neural network; and
the display device configured to receive the ultrasound image via the second communication link and display the ultrasound image.

2. The ultrasound system as described in claim 1, wherein the processor system is implemented to, when the mobile computing device is supported by the docking station, disable the first communication link and enable a wireless coupling of the ultrasound scanner to the display device via a third communication link.

3. The ultrasound system as described in claim 1, wherein the docking station is implemented to provide power to the mobile computing device when the mobile computing device is supported by the docking station.

4. The ultrasound system as described in claim 1, wherein the docking station includes the processor system that includes processing resources implemented to generate the additional ultrasound features.

5. The ultrasound system as described in claim 1, wherein the processor system is implemented to transfer a medical worksheet displayed on the display device to the mobile computing device, and the mobile computing device is implemented to display the medical worksheet.

6. The ultrasound system as described in claim 5, wherein the transfer of the medical worksheet is responsive to a user input, the ultrasound scanner is implemented to transmit the ultrasound and receive the reflections as part of an ultrasound examination, and the mobile computing device is implemented to display the medical worksheet when the ultrasound examination is completed and when the mobile computing device is unsupported by the docking station.

7. The ultrasound system as described in claim 5, wherein the mobile computing device is implemented to, responsive to the transfer, populate the medical worksheet with ultrasound data generated based on the reflections of the ultrasound.

8. The ultrasound system as described in claim 1, wherein the mobile computing device is implemented to display user interfaces for controlling the ultrasound system including a first user interface when the mobile computing device is supported by the docking station and a second user interface when the mobile computing device is unsupported by the docking station.

9. The ultrasound system as described in claim 8, wherein the display device is implemented to display a third user interface for controlling the ultrasound system, the third user interface including at least one ultrasound control that is not included in the first user interface.

10. The ultrasound system as described in claim 8, wherein the first user interface includes at least one ultrasound control that is not included in the second user interface.

11. The ultrasound system as described in claim 8, wherein the second user interface includes at least one ultrasound control that is not included in the first user interface.

12. The ultrasound system as described in claim 1, wherein the docking station is implemented to be removably attached to the ultrasound scanner for transport of the ultrasound scanner and the docking station as a single unit.

13. An ultrasound system comprising:
an ultrasound scanner configured to transmit ultrasound at a patient anatomy and receive reflections of the ultrasound from the patient anatomy;
a mobile computing device configured to be coupled to the ultrasound scanner;
a display device configured to display an ultrasound image that is generated based on the reflections of the ultrasound;
a memory coupled to the display device;
a docking station coupled to the display device and the memory and configured to support the mobile computing device, the mobile computing device configured to display, on the display device, a first user interface including a first ultrasound control panel for controlling first ultrasound features of the ultrasound system when supported by the docking station and to display, on the display device, a second user interface including the first ultrasound control panel and an additional ultrasound control panel for controlling additional ultrasound features stored in the memory of the ultrasound system when the mobile computing device is unsupported by the docking station, wherein the additional ultrasound control panel is not included in the first user interface.

14. The ultrasound system as described in claim 13, wherein the first user interface includes at least one ultrasound control for controlling the ultrasound system, wherein the at least one ultrasound control is not included in the second user interface.

15. The ultrasound system as described in claim 13, wherein the display device is implemented to:
  display a third user interface that is configured to display a medical worksheet;
  receive a user input; and
  transfer, responsive to the user input, the medical worksheet to the mobile computing device for display of the medical worksheet on the mobile computing device.

16. The ultrasound system as described in claim 15, wherein the mobile computing device is implemented to transfer the medical worksheet to a medical records archiver.

17. The ultrasound system as described in claim 16, wherein the mobile computing device is implemented to receive medical records from the medical records archiver.

18. An ultrasound system comprising:
  an ultrasound scanner configured to transmit ultrasound at a patient anatomy and receive ultrasound data based on reflections of the ultrasound from the patient anatomy as part of an ultrasound examination;
  a memory coupled to the ultrasound scanner to store the ultrasound data;
  a first display device coupled to the memory and configured to, during the ultrasound examination:
    display the ultrasound data including an ultrasound image and a medical worksheet on the first display device; and
    transfer the ultrasound data displayed on the first display device to a mobile computing device;
  the mobile computing device configured to display, on a second display device, the ultrasound image, the medical worksheet and a measurement and label panel for at least one of labeling and measurement of the ultrasound image subsequent to the ultrasound examination.

19. The ultrasound system as described in claim 18, further comprising a docking station implemented to, during the ultrasound examination, support the mobile computing device and couple the ultrasound scanner to the first display device.

* * * * *